(12) United States Patent
Wang et al.

(10) Patent No.: US 8,680,155 B2
(45) Date of Patent: Mar. 25, 2014

(54) SYNTHESIS AND ANTITUMOR ACTIVITY OF NOVEL BIS(BENZYLIDENE-BENZENAMINE)DISULFIDES

(75) Inventors: Jeh-Jeng Wang, Kaohsiung (TW);
Wan-Ping Hu, Kaohsiung (TW);
Wei-Sheng Lo, Kaohsiung (TW)

(73) Assignee: Kaohsiung Medical University (TW)

( * ) Notice: Subject to any disclaimer, the term of this patent is extended or adjusted under 35 U.S.C. 154(b) by 163 days.

(21) Appl. No.: 13/190,845

(22) Filed: Jul. 26, 2011

(65) Prior Publication Data

US 2012/0283475 A1  Nov. 8, 2012

(30) Foreign Application Priority Data

May 2, 2011  (TW) .............. 100115387 A

(51) Int. Cl.
*A61K 31/13* (2006.01)
*C07C 251/02* (2006.01)

(52) U.S. Cl.
USPC .......................................... 514/641; 564/272

(58) Field of Classification Search
USPC .......................................... 514/641; 564/272
See application file for complete search history.

(56) References Cited

PUBLICATIONS

Schaeffer et al, J. of Org. Chem, 1967, 32(2), 392-5.*
Ali et al., "Oxidation of thiols to disulfides with molecular bromine on hydrated silica gel support," Tetrahedron Letters (2002) 43:6271-6273.
Karami et al., "Urea-hydrogen peroxide (UHP) oxidation of thiols to the corresponding disulfides promoted by maleic anhydrides as mediator," Molecules (2005) 10:1358-1363.
Peterson et al., "Procaspase-3 activation as an anti-cancer strategy: structure-activity relationship of procaspaseactivating compound 1 (PAC-1) and its cellular co-localization with capase-3," J. Med. Chem (2009) 52(18);5721-5731.
Shinkai et al., "Bis(2-(acylamino)phenyl) disfulides, 2-(acrylamino)bezenethiols, and S-(2-(acrylamino)phenyl alkanethioates as novel inhibitors of cholesteryl ester transfer protein," J. Med. Chem. (2000) 43:3566-3572.
Lo et al., "Synthesis of sulfur-sulfur bond formation from thioamides promoted fby 2,3-dichloro-5,6-dicyanobenzoquinone," Org. Lett. (2010) 12(23):5570-5572.
Beerhei et al., "Idenactivation of the Human Papillomavirus-16 E6 Oncoprotein by Organic Disulfides," Bioorganic and Medicinal Chemistry 8 (2000) 2549.
Schaeffer et al., "Synthesis, Stability, and Sulfur-Elimination Reactions of Some bis(N-arylimidoyl) disulfides," J. Org. Chem., 32 (2) pp. 392-395 (1967).

\* cited by examiner

*Primary Examiner* — Shailendra Kumar
(74) *Attorney, Agent, or Firm* — Volpe and Koenig, P.C.

(57) ABSTRACT

Novel synthetic bis(benzylidene-benzenamine)disulfides and the preparation method are disclosed in the present invention. These compounds are afforded with the oxidizing reagent at low temperature and short time period via intramolecular coupling reaction. In vitro experiments have been revealed that bis-disulfides are cytotoxic to cancer cells, especially human breast cancer cells MCF-7. Additionally, bis-disulfides arrest the cell cycle at sub-G1 phase and increase p38 phosphorylation to result in apoptosis. Bis-disulfides also inhibit growth of murine melanoma B16 cells but have no cytotoxicity to human fibroblasts. Bis-disulfides also can reduce murine melanoma size in the mouse model. The prepared compounds of the invention would be applicable in anticancer and anti-tumor therapies.

11 Claims, 2 Drawing Sheets

SYNTHESIS AND ANTITUMOR ACTIVITY OF NOVEL BIS(BENZYLIDENE-BENZENAMINE)DISULFIDES

CROSS-REFERENCE TO RELATED APPLICATION AND CLAIM OF PRIORITY

The application claims the benefit of Taiwan Patent Application No. 100115387, filed on May 2, 2011, in the Taiwan Intellectual Property Office, the disclosures of which are incorporated herein in their entirety by reference.

FIELD OF THE INVENTION

The present invention relates to a synthetic method of a pharmaceutical composition for treating cancer. In particular, the present invention relates to a pharmaceutical composition including bis(benzylidene-benzenamine)disulfide and the synthetic method thereof.

BACKGROUND OF THE INVENTION

Cancer has become the leading cause of death in Taiwan for a long time, and thus diagnosis, therapy and pursuance of cancer are extremely important to nationals' health and lives. Cancer therapy mainly depends on surgical therapy, radiation therapy and chemotherapy. Surgical therapy usually is made by cutting off cancer cells or cancer tissues as well as the surrounding normal tissues and lymphs and administrating with radiation therapy or chemotherapy according to the cancer properties so as to avoid cancer recurrence. However, chemotherapeutic drugs and high-energy radiation also destroy normal cells and tissues and generate side effects.

Furthermore, cancer therapy drugs can be grouped as cytotoxic therapy, hormonal therapy, targeted therapy and cancer support therapy. Drugs for cancer support therapy are used to reduce the derived side effects. Drugs for cytotoxic therapy on cancer cells can include cytotoxic therapy, hormonal therapy and targeted therapy. The aforementioned chemotherapeutic drugs are involved in these three therapies.

Drugs for cytotoxicity on cancer cells include alkylating agents, antimetabolites, microtubule stimulants (e.g. Paclitaxel), microtubule inhibitors (e.g. vinca alkaloid), cytotoxic antibiotics and DNA topoisomerase inhibitors, etc. Types of hormonal therapy drugs include hormone antagonists and hormone agonists for influencing hormone functions, or aromatase inhibitors for influencing hormone metabolism. Types of targeted therapy drugs include angiogenesis inhibitors, epidermal growth factor receptor (EGFR) inhibitors, immunotherapy agents, apoptosis agonists, and so on. Each of the aforementioned anticancer drugs has a specific effect but also generates side effects. Therefore, searching for novel anticancer drugs remains an R&D issue to scientists.

In the past, molecules containing a disulfide moiety play a vital role in chemistry and biochemistry. For instance, Shinkai et al. (2000) published that various disulfides were synthesized to show inhibition effects on cholesteryl ester transfer protein in human sera. Peterson et al. suggested that the condensation reaction was made on hydrazide and aldehyde carrying sulfhydryl group to synthesize molecules containing sulfur-sulfur bond and the molecule has biological activities such as anticancer and so on (Peterson et al., 2009.). In addition, oxidation of thiols was made using halide and hydrogen peroxide to generate disulfide molecule (Ali and McDermott, 2002; Karami et al., 2005).

It is therefore attempted by the applicant to deal with the above situation encountered in the prior art.

SUMMARY OF THE INVENTION

The preparation of bis(benzylidene-benzenamine)disulfide in the invention does not charge the high cost of raw material mercaptan, and has advantages of free radical reactions high reactivity, less susceptible to the impact of three-dimensional obstacles, rate fast and mild reaction conditions and the organic solution can be carried out in response to neutral.

The invention provides a pharmaceutical composition for treating cancer, including bis(benzylidene-benzenamine)disulfide represented by formula I:

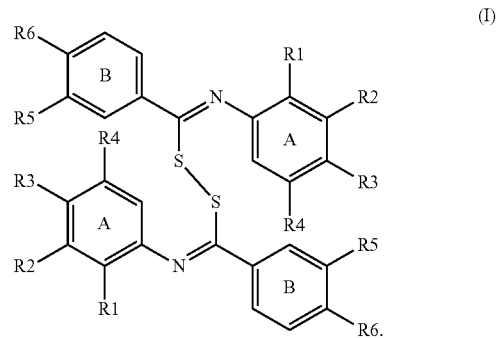

(I)

Ring A includes an R1, an R2, an R3 and an R4 bound thereon, R1 is hydrogen (H) or alkyl group ($-C_xH_{2x+1}$, x=1~6), R2 is H or nitrite ($-NO_2$), R3 is H, $-NO_2$, alkyl halide group ($-C_pH_qX_r$, where p=1~6, and q+r=2p+1), halide (X) or alkyl group ($-C_yH_{2y+1}$, where y=1~6), and R4 is H or $-NO_2$. Ring B includes an R5 and an R6 bound thereon, R5 is H, alkyl group ($-C_zH_{2z-1}$, where z=1~6) or alkoxy group ($-OC_nH_{2n+1}$, where n=1~6), R6 is H, $-NO_2$, alkyl halide group ($-C_sH_tX_u$, where s=1~6, and t+u=2s+1) or X, X is indicated to fluoride (F), chloride (Cl), bromide (Br) and iodine (I), and p, q, r, s, t and u are positive integers.

The cancer is referred to non-small cell lung cancer, colon cancer, central nervous system cancer, melanoma, ovarian cancer and breast cancer.

The invention provides a preparation method corresponding to the above pharmaceutical composition, including a step of synthesizing two thiobenzamides (formula II) to form bis(benzylidene-benzenamine)disulfide (formula I) with an oxidizing reagent, wherein the substituent groups, R1 to R6 are illustrated as above.

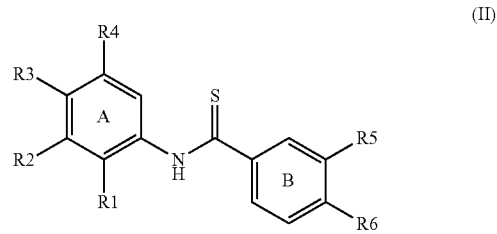

(II)

The invention provides a pharmaceutical composition for treating cancer, including bis(benzylidene-benzenamine)disulfide represented by formula III:

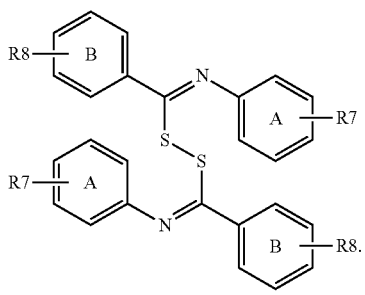

(III)

Ring A has four sequentially bound carbon atoms, respectively bound with four R7s, each R7 is a first electron-withdrawing group (EWG) or H, ring B has a para-carbon atom and a meta-carbon atom respectively bound with two R8s, and each R8 is a second EWG, an electron-donating group (EDG) or H.

Preferably, the first EWG and the second EWG respectively is alkyl group ($—C_xH_{2x+1}$, where x=1~6 for the first EWG; $—C_yH_{2y+1}$, where y=1~6 for the second EWG), $—NO_2$, alkyl halide group ($—C_aX_{2a+1}$, where a=1~6 for the first EWG; $—C_bX_{2b+1}$, where b=1~6 for the second WEG) or X, X is F, Cl, Br or I, and "x", "y", "a" and "b" are positive integers. The EDG is alkoxy group ($—OC_nH_{2n+1}$, where n=1~6).

The invention provides a preparation method of a pharmaceutical composition (which includes bis(benzylidene-benzenamine)disulfide, formula III) for treating cancer, and the method includes a step of synthesizing bis(benzylidene-benzenamine)disulfide from two thiobenzamides with an oxidizing reagent, wherein each of two thiobenzamides is represented by formula IV:

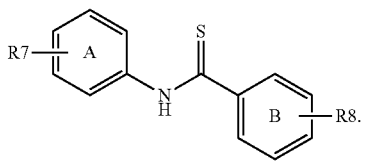

(IV)

The substituent groups, R7 and R8 are, on ring A and ring B respectively are illustrated as above.

Preferably, the preparation method further includes a step of forming a disulfide bond between the two thiobenzamides.

The oxidizing reagent can be 2,3-dichloro-5,6-dicyanobenzoquinone (DDQ), cerium(IV)ammonium nitrate (CAN), Dess-Martin periodinane (DMP) or phenyliodine (III) bis(trifluoroacetate) (PIFA). The oxidizing reagent is dissolved in a solvent such as dichloromethane, methanol and acetonitrile.

The synthesizing step is performed at 0° C. to 30° C. for 20 minutes to 120 minutes, preferably, at 0° C. to 28° C. within 20 minutes.

The above objectives and advantages of the present invention will become more readily apparent to those ordinarily skilled in the art after reviewing the following detailed descriptions and accompanying drawings.

DETAILED DESCRIPTION OF THE PREFERRED EMBODIMENT

Figure 1:
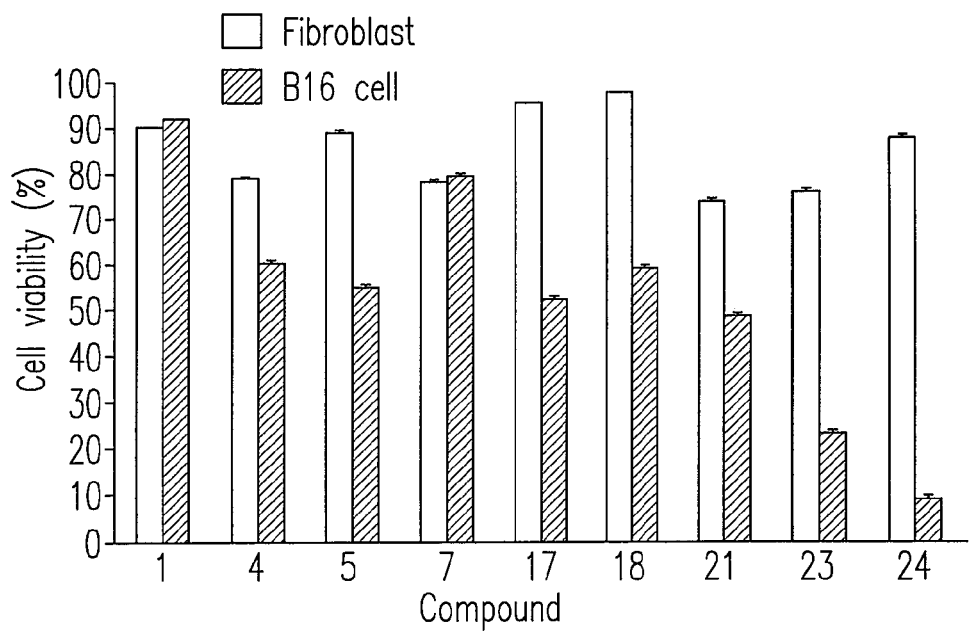
FIG. 1 illustrates a diagram showing growth inhibition of various compounds of the invention on human dermal fibroblast and B16 cells.

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

Experiment 1: Preparation of bis(benzylidene-benzenamine)-disulfide

The key point of the invention is to synthesize bis(benzylidene-benzenamine)disulfide (hereinafter "disulfide"; formula III) having disulfide bond therein from two thiobenzamides (formula IV) using oxidizing reagent via the inter-molecular coupling reaction, which is represented as reaction formula I.

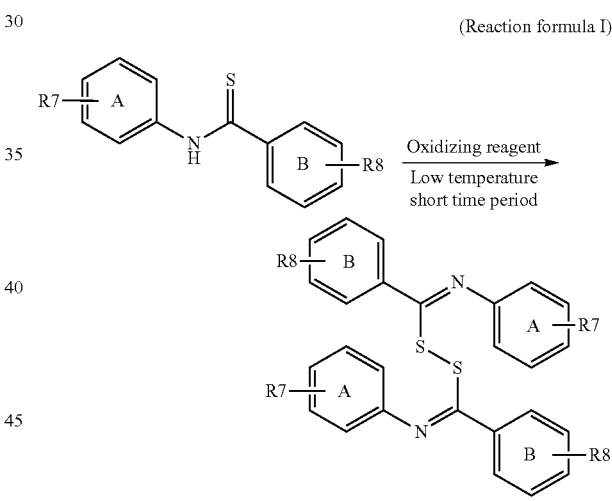

(Reaction formula I)

Each R7 respectively was bound to four neighboring carbon atoms of ring A. That is, each R7 sequentially was bound to para-carbon, meta-carbon, ortho-carbon and another para-carbon, and each R7 could be an electron-withdrawing group (EWG) or hydrogen (H). Furthermore, each R8 respectively was bound to ortho-carbon and meta-carbon of ring B, and each R8 could be an EWG, an electron-donating group (EDG) or H.

The oxidizing reagent of the invention could be 2,3-dichloro-5,6-dicyanobenzoquinone (DDQ), cerium(IV)ammonium nitrate (CAN), Dess-Martin periodinane (DMP), phenyliodine(III) bis(trifluoroacetate) (PIFA) or potassium ferricyanide ($K_3Fe(CN)_6$), and these oxidizing reagent could be dissolved in dichloromethane ($CH_2Cl_2$), methanol (MeOH) or acetonitrile ($CH_3CN$) based on the nature of the oxidizing reagent.

The inter-molecular coupling reaction of the invention was made at low temperature, 0° C. to 30° C., during short time period (20 minutes to 120 minutes). A best embodiment of the invention was performed at 0° C. to 28° C. within 20 minutes.

Please refer to Table 1, which is the optimization of sulfur-sulfur bond formation for thiobenzamides with various oxidizing reagents. Ring B of thiobenzamide had ortho-nitrite (4-NO$_2$) and para-methyl group (3-CH$_3$). Compound 1 with 88% yield was afforded at the conditions that DDQ (1.2 equivalents) was dissolved in CH$_2$Cl$_2$ (0° C.), the temperature was 0° C. to 28° C. and the reaction time was 20 minutes. However, no side product was produced (entry 1, Table 1). However, if DDQ was dissolved in MeOH and other experimental parameters were the same, compound 1 with 62% yield and intramolecular cyclization side product (formula VI) in 31% yield was afforded (entry 2, Table 1).

TABLE 1

Optimization of S—S bond formation with various oxidizing reagents (VI)

| Entry | Reagent | E-quiv. | Solvent | Temp. (° C.) | Time (Min) | Yield of compound 1 (%) | Yield of formula VI by-product (%) |
|---|---|---|---|---|---|---|---|
| 1 | DDQ | 1.2 | CH$_2$Cl$_2$ | 0~28 | 20 | 88 | 0 |
| 2 | DDQ | 1.2 | MeOH | 0~28 | 20 | 62 | 31 |
| 3 | CAN | 4.2 | CH$_3$CN | 0 | 30 | 43 | 55 |
| 4 | CAN | 4.2 | MeOH | 0 | 30 | 57 | 33 |
| 5 | DMP | 1.2 | CH$_2$Cl$_2$ | 0 | 40 | 42 | 46 |
| 6 | DMP | 2.2 | MeOH | 0 | 30 | 12 | 54 |
| 7 | PIFA | 1.2 | CH$_2$Cl$_2$ | 28 | 30 | 17 | 58 |
| 8 | PIFA | 2.2 | CH$_3$CN | 0 | 90 | 14 | 64 |
| 9 | K$_3$Fe(CN)$_6$ | 4 | CH$_3$CN | 0 | 120 | 0 | 72 |
| 10 | K$_3$Fe(CN)$_6$ | 4 | EtOH | Reflux | 90 | 0 | 0 |

Please refer to Table 1, if CAN (4.2 equiv.) was dissolved in CH$_3$CN (0° C.) and reacted with thiobenzamides for 30 minutes, the ratio of compound 1 and side product (formula VI) was 1:1 (entry 3, Table 1), whereas reaction in MeOH gave compound 1 in 57% yield and side product (formula VI) in 33% yield (entry 4, Table 1). If hypervalent iodo reagent, DMP or PIFA, was used as notable oxidant, yield of side product (formula VI) was higher than that of compound 1, and side product became the major product (entries 5 to 8, Table 1). If K$_3$Fe(CN)$_6$ (4 equiv.) was dissolved in CH$_3$CN (0° C.) and reacted with thiobenzamides for 2 hours, side product (formula VI) had 72% yield but compound 1 was not given (entry 9, Table 1). In addition, increasing the polarity of solvent (ethanol) and reaction temperature with K$_3$Fe(CN)$_6$, no reaction was observed, and the starting material was recovered (entry 10, Table 1).

Next, disulfides with various substituents on rings A and B were designed and synthesized on the basis of the optimal conditions for compound 1. As aforementioned, each R7 on ring A was designated as EWG or H, and ortho-carbon and meta carbon on ring B respectively could be bound with R8 substituent such as EWG, EDG or H. For the convenient description, reaction formula I was rewrote as reaction formula II, wherein R7 on ring A was indicated to R1, R2, R3 and R4 substituents which were represented as para-, meta-, ortho-, and another meta-substituted groups, respectively, and R8 on ring B was indicated to R5 and R6 substituents which were represented as meta- and ortho-substituted groups, respectively.

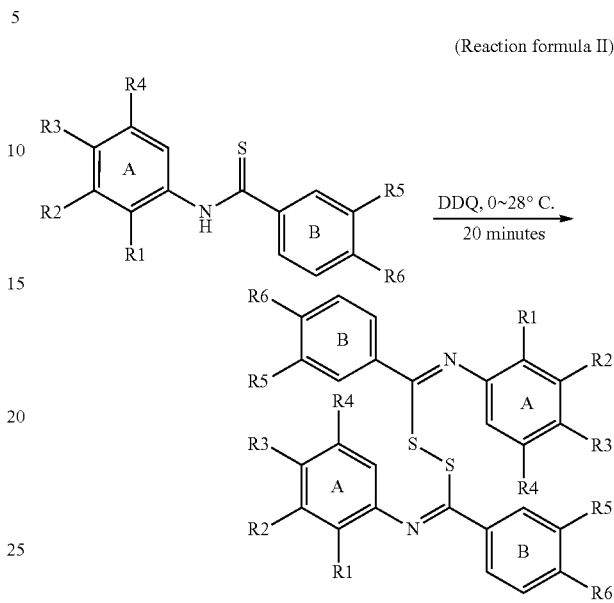

(Reaction formula II)

Please refer to Table 2, which are compounds 1 to 24 formed with DDQ in the present invention. In Table 2, ring A of compound 1 only bound with H without binding with other substituents, and nitrite (—NO$_2$) was borne on R6 of ring B as strong EWG. R3 on ring A of compounds 2 and 3 was bound with nitrite (—NO$_2$) as strong EWG, R5 of ring A was bound with methoxy (—OCH$_3$), and thus compounds 2 and 3 also had relatively high yield (74%). R3 on ring A of compounds 4 to 7 was designed to bind with relatively weak EWG (i.e. —Cl or —CF$_3$), R6 on ring B was strong EWG (—NO$_2$), and thus compounds 4 to 7 also had relatively high yield (78% to 82%). As to compounds 8 to 15, ortho-substituent (R3) on ring A was designed as nitrite for withdrawing electron, ortho-substituent (R6) on ring B was designed as weaker electron-withdrawing halide or trifluoromethyl group, and their yields were ranged 71% to 83%. With regard to compounds 16 to 24, R2 or R4 meta-substituent on ring A was strong EWG (—NO$_2$), R3 ortho-substituent was weak EWG (such as —Cl, —CF$_3$ or —CH$_3$), R6 substituent on ring B was weaker electron-withdrawing halide or trifluoromethyl group, and thus compounds 16 to 24 still had relatively high yields (72% to 86%).

TABLE 2

Compounds 1 to 24 formed with DDQ in the present invention

| Compound | R1 | R2 | R3 | R4 | R5 | R6 | Yield (%) |
|---|---|---|---|---|---|---|---|
| 1 | H | H | H | H | CH$_3$ | NO$_2$ | 88 |
| 2 | H | H | NO$_2$ | H | OCH$_3$ | H | 74 |
| 3 | CH$_3$ | H | NO$_2$ | H | OCH$_3$ | H | 74 |
| 4 | H | H | CF$_3$ | H | H | NO$_2$ | 76 |
| 5 | H | H | Cl | H | H | NO$_2$ | 74 |
| 6 | H | H | CF$_3$ | H | CH$_3$ | NO$_2$ | 82 |
| 7 | H | H | Cl | H | CH$_3$ | NO$_2$ | 77 |
| 8 | H | H | NO$_2$ | H | H | CF$_3$ | 75 |
| 9 | H | H | NO$_2$ | H | H | F | 76 |
| 10 | H | H | NO$_2$ | H | H | Cl | 72 |
| 11 | H | H | NO$_2$ | H | H | Br | 72 |
| 12 | CH$_3$ | H | NO$_2$ | H | H | CF$_3$ | 81 |

TABLE 2-continued

Compounds 1 to 24 formed with DDQ in the present invention

| Compound | R1 | R2 | R3 | R4 | R5 | R6 | Yield (%) |
|---|---|---|---|---|---|---|---|
| 13 | $CH_3$ | H | $NO_2$ | H | H | F | 79 |
| 14 | $CH_3$ | H | $NO_2$ | H | H | Cl | 83 |
| 15 | $CH_3$ | H | $NO_2$ | H | H | Br | 71 |
| 16 | H | $NO_2$ | Cl | H | H | $CF_3$ | 72 |
| 17 | H | $NO_2$ | $CH_3$ | H | H | $CF_3$ | 72 |
| 18 | $CH_3$ | $NO_2$ | H | H | H | F | 83 |
| 19 | $CH_3$ | $NO_2$ | H | H | H | Cl | 74 |
| 20 | $CH_3$ | H | H | $NO_2$ | H | $CF_3$ | 86 |
| 21 | $CH_3$ | H | H | $NO_2$ | H | F | 84 |
| 22 | $CH_3$ | H | H | $NO_2$ | H | Cl | 81 |
| 23 | H | $NO_2$ | F | H | H | $CF_3$ | 78 |
| 24 | $CH_3$ | $NO_2$ | H | H | H | $CF_3$ | 82 |

When ring A of the disulfide molecule did not bear other substituents and its ring B had EWG, its yield was 76%. Therefore, substituents on rings A and B play an important role in disulfide bond formation.

The disulfides of the invention was synthesized using the scheme of reaction formula 1, and reaction formula 2 is the more detail synthetic scheme. The substituents shown in Table 1 were the best embodiments. Nevertheless, with various experiments, it is proved that the carbon number of alkyl group, alkyl halide group and alkoxy group on rings A and B can be one or more than one, and the carbon number preferably is 6 or less than 6, so that the disulfides of the invention can be successfully synthesized.

Experiment 2: Cytotoxicity of Compounds to Cancer Cells

For confirming the cytotoxicity of bis(benzylidene-benzenamine)disulfides of the invention on various cancer cells, the well known MTT (3-(4,5-dimethylthiazol-2-yl)-2,5-diphenyltetrazolium bromide) colorimetric assay in this art was performed, and the method was not detailedly described herein. Please refer to Table 3, compound 12 was selected from compounds 1 to 24 to proceed cytotoxicity experiment. It could be known from Table 3 that the mean 50% growth inhibition ($GI_{50}$) value for compound 12 was 0.372 µM, indicating that compound 12 has the potential for use as a highly potent broad-spectrum anticancer compound or reagent to inhibit the growth of a variety of cancer cell lines.

TABLE 3

In vitro cytotoxicity of compound 12 in selected cancer cell lines

| Cell line | $GI_{50}$ (µM) |
|---|---|
| Non-small cell lung cancer | |
| HOP-92 | 0.175 |
| NCI-H226 | 0.427 |
| Colon cancer | |
| HCT-15 | 0.388 |
| Central nervous system cancer | |
| SNB-75 | 0.141 |
| Melanoma | |
| LOX MVI | 0.304 |
| MALME-3M | 0.252 |
| SK-MEL-5 | 0.262 |
| Ovarian cancer | |
| IGROV1 | 0.217 |
| Breast cancer | |
| T-47D | 0.221 |
| Mean | 0.372 |

However, cancer or tumor administrated by the disulfides of the invention does not limit in the types of Table 3, one skilled in the art has motivation to administrate the disulfides in subjects who suffers cancer or carcinoma, such as sarcoma, leukemia, stomach carcinoma, lymphoma, skin cancer, testiculus cancer, stomach cancer, pancreatic cancer, urinary colorectal cancer, head and neck cancer, brain cancer, esophageal cancer, urinary cancer, adrenocortical carcinoma, lung cancer, bronchial carcinoma, endometrial cancer, nasopharyngeal carcinoma, cervical cancer, liver cancer, carcinoma of unknown primary site and so on, or cells of aforementioned cancers or carcinomas, and subjects can be humans or animals.

Next, in vitro cytotoxicity of the multiple compounds in various cell lines was evaluated, which also was performed using MTT colorimetric assay. Please refer to Table 4, each of compounds showed various inhibition effect on the selected cancer cells, indicating that disulfides prepared in the invention can be applied on inhibiting growth of cancer cells and shows the cytotoxicity to cancer cells. Comparing breast cancer cells MCF-7 with other cancer cells, most selected compounds had higher inhibition activity to MCF-7 cells. Therefore, breast cancer cells MCF-7 were chosen to be the research target in the following experiments.

In addition, for recognizing whether the prepared disulfides had cytotoxicity to normal cells and murine cells, human dermal fibroblasts and mouse melanoma cells B16 were selected as the models using MTT colorimetric assay. First, fibroblasts or B16 cells were seeded in 96-well culture plate at 2500 cells per well and cultivated overnight until cell attachment. Each compound (10 µM) was added into the culture media in triplicate and incubated for 48 hours, and finally MTT reagent was added into each well to detect absorbance.

Please refer to FIG. 1, which illustrates the growth inhibition of various compounds to human dermal fibroblast and B16 cells. It could be known from FIG. 1 that preferential apoptosis in human fibroblasts was not significantly made by each prepared compound but significantly made in murine melanoma B16 by compound such as compounds 23 and 24.

Experiment 3: Influence of Compounds to Cell Cycle

This experiment was performed by treating breast cancer cells MCF-7 with compounds, and then cell cycle was analyzed using flow cytometry known by the skilled person in the art. Firstly, breast cancer cells MCF-7 were treated with the prepared compounds (5 µM) for 24 hours and stained with propidium iodide (PI). Approximately 10000 cells from each sample were analyzed with FACScan flow cytometer and software. Data represented that the prepared compounds 4, 5, 7, 18, 21, 23 and 24 resulted in MCF-7 cells having a hypodiploid DNA content, indicating MCF-7 cells were arrested in sub-G1 phase. The sub-G1 DNA Peaks for compounds 4, 5, 7, 18, 21, 23 and 24 were 20.64%, 17.92%, 26.22%, 11.95%, 19.85%, 4.35% and 33.89% respectively (data not shown), while the sub-G1 DNA peak for control (without any drug treatment) was 11.54%.

Experiment 4: Apoptosis-Related Protein Expression

Figure 2:
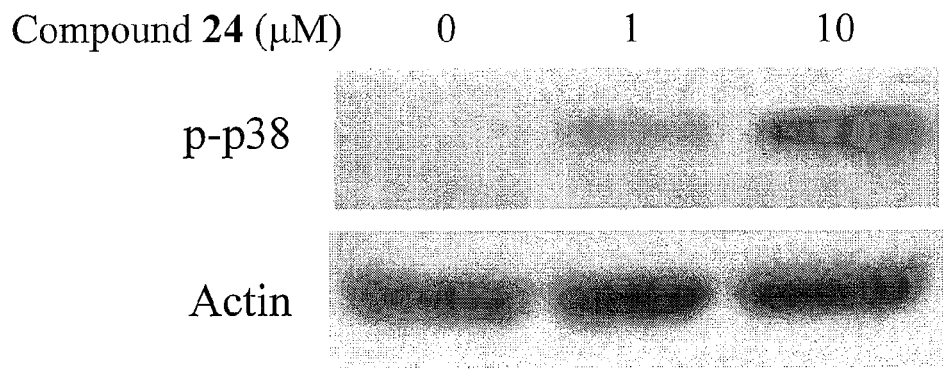
FIG. 2 illustrates an immunoblot analysis showing the effect of the present compound 24 with different concentrations on phosphorylated p38 protein expression on MCF-7 cells.

P38 protein in p38 mitogen-activated protein kinase (MAPK) pathway was chosen to be the index of apoptosis in this experiment, and phosphorylated p38 expression was evaluated using immunoblotting assay known by the skilled person in the art. Cellular protein was harvested after the 24-hour treatment of compound 24 on MCF-7 cells, and then resolved with sodium dodecyl sulfate (SDS)-polyacrylamide gel electrophoresis and developed using immunoblotting. Please refer to FIG. 2, the phosphorylation of p38 protein was dependent on the concentration of compound 24. The higher compound 24 resulted in the higher expression of phosphorylated p38 and higher apoptosis of MCF-7 cells. In combination with aforementioned experimental results, compound 24 and other compounds could induce cancer cell apoptosis.

Experiment 5: Antitumor Activity of Compounds in Tumor-Bearing Mice

Firstly, a total of $5 \times 10^6$ melanoma cells B16 were inoculated into female C57BL/6 mice (about 19~21 grams/7 to 9 weeks). The subcutaneous inoculation of tumor cells resulted in tumor generation at the injection site. When tumor reached about 4 mm×4 mm in diameter, mice were separated into groups. Each group had four mice in each experiment. Tumor volume were majored by calipers each two days after compound injection into each sole of feet of mice or without compound injection (control), and tumor volume was calculated by following formula:

$$\text{Tumor volume} = \frac{1}{2} \times \text{length} \times \text{width} \qquad \text{(Equation I)}$$

Figure 3:
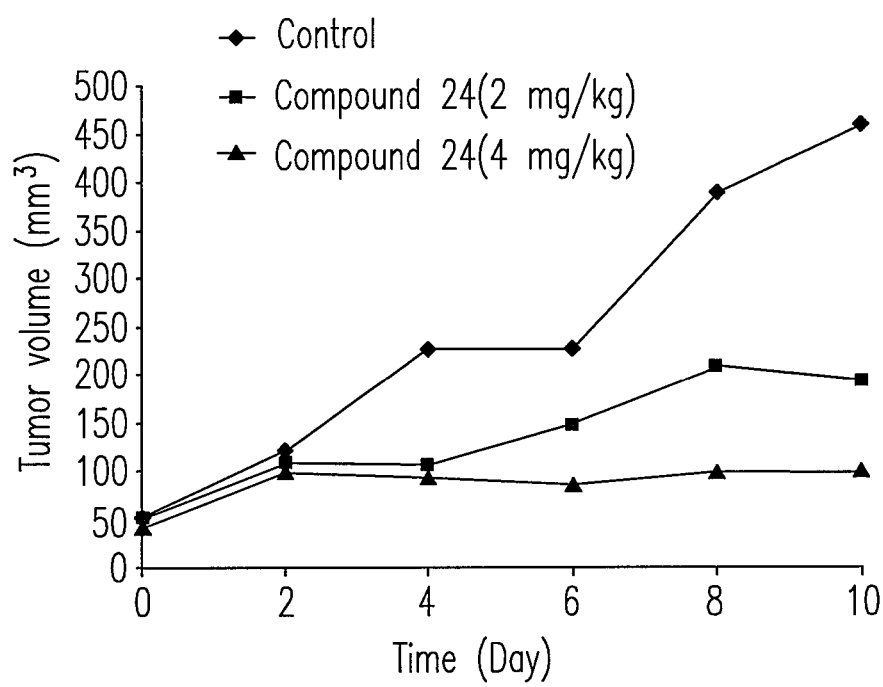
FIG. 3 illustrates an diagram showing the tumor size-time relationship that compound 24 of the invention inhibits the tumor growth of B16 cells-injected C57BL/6 mice.

Please refer to FIG. 3, the tumor volume of the untreated control group markedly increased in a time-dependent manner. However, the tumor volume was significantly suppressed compared to the untreated group by compound 24 (4 mg/kg) treatment, and the tumor volume was not markedly increased with compound 24 (2 mg/kg) treatment.

In conclusion, disulfides with sulfur-sulfur bond and high yield were synthesized using oxidizing reagent (such as DDQ) in the present invention, and the synthesized disulfides were proved to inhibit growth of cancer cells and promote apoptosis and further administrate in cancer treatment on animal model. In addition, the present invention also can be applied in the synthetic method of forming sulfur-sulfur bond on other molecules with different thiol substituents and the various analogs.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

TABLE 4

| | Compounds against human-derived cancer cell lines in vitro | | | | | | | | |
|---|---|---|---|---|---|---|---|---|---|
| | Survival (% control) of compound (10 μM) | | | | | | | | |
| Cell line | 1 | 4 | 5 | 7 | 17 | 18 | 21 | 23 | 24 |
| Melanoma | | | | | | | | | |
| A2058 | | 92.6 ± 0.05 | 97.5 ± 0.02 | 99.6 ± 0.02 | | 95.9 ± 0.02 | 76.3 ± 0.15 | 93.2 ± 0.04 | 34.9 ± 0.42 |
| A375 | 90.3 ± 0.05 | 84.6 ± 0.08 | 79.4 ± 0.11 | 92.4 ± 0.04 | 103.2 ± 0.02 | 91.5 ± 0.04 | 81.1 ± 0.10 | 94.3 ± 0.03 | 59.5 ± 0.22 |
| Kidney cancer | | | | | | | | | |
| 293T | 76.5 ± 0.19 | 64.6 ± 0.28 | 70.9 ± 0.24 | 71.2 ± 0.23 | 75.3 ± 0.21 | 71.1 ± 0.23 | 32.8 ± 0.52 | 57.8 ± 0.33 | 24.2 ± 0.59 |
| Lung Cancer | | | | | | | | | |
| H1335 | 69.8 ± 0.13 | 66.0 ± 0.14 | 75.8 ± 0.10 | 67.4 ± 0.13 | 81.4 ± 0.08 | 70.0 ± 0.13 | 80.6 ± 0.08 | 80.2 ± 0.08 | 26.0 ± 0.32 |
| A549 | 71.5 ± 0.09 | 65.4 ± 0.11 | 82.4 ± 0.06 | 78.7 ± 0.07 | 76.9 ± 0.07 | 75.5 ± 0.08 | 62.1 ± 0.12 | 64.4 ± 0.12 | 53.4 ± 0.15 |
| Breast cancer | | | | | | | | | |
| MCF-7 | | 59.6 ± 0.28 | 54.3 ± 0.32 | 51.7 ± 0.34 | | 33.1 ± 0.47 | 13.8 ± 0.60 | 57.1 ± 0.30 | 8.6 ± 0.64 |
| Oral cancer | | | | | | | | | |
| Cal-27 | 100.9 ± 0.09 | 102.5 ± 0.06 | 100.1 ± 0.07 | 101.7 ± 0.09 | 107.1 ± 0.08 | 94.9 ± 0.07 | 76.6 ± 0.20 | 92.4 ± 0.16 | 73.5 ± 0.22 |
| Ca-922 | 80.8 ± 0.08 | 80.1 ± 0.08 | 79.4 ± 0.08 | 96.2 ± 0.02 | 82.1 ± 0.07 | 79.4 ± 0.09 | 66.7 ± 0.13 | 65.8 ± 0.14 | 45.5 ± 0.22 |

What is claimed is:

1. A pharmaceutical composition for treating a cancer, comprising a bis(benzylidene-benzenamine)disulfide represented by formula I:

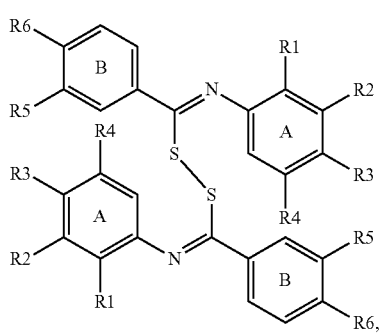

wherein the ring A comprises an R1, an R2, an R3 and an R4 bound thereon, R1 is one selected from the group consisting of a hydrogen, $CH_3$, $C_2H_5$, $C_3H_7$, $C_4H_9$, $C_5H_{11}$ and $C_6H_{13}$, R2 is one of a hydrogen and a nitrite, R3 is one selected from the group consisting of a hydrogen, a nitrite, $CF_3$, a halide, $CH_3$, $C_2H_5$, $C_3H_7$, $C_4H_9$, $C_5H_{11}$ and $C_6H_{13}$, R4 is one of a hydrogen and a nitrite, the ring B comprises an R5 and an R6 bound thereon, R5 is one selected from the group consisting of a hydrogen, $CH_3$, $C_2H_5$, $C_3H_7$, $C_4H_9$, $C_5H_{11}$, $C_6H_{13}$, $OCH_3$, $OC_2H_5$, $OC_3H_7$, $OC_4H_9$, $OC_5H_{11}$ and $OC_6H_{13}$, R6 is one selected from the group consisting of a hydrogen, a nitrite, $CF_3$ and a halide and the halide is selected from the group consisting of fluoride, chloride, bromide and iodine.

2. The pharmaceutical composition according to claim 1, wherein the cancer is selected from a group consisting of a non-small cell lung cancer, a colon cancer, a central nervous system cancer, a melanoma, an ovarian cancer and a breast cancer.

3. A pharmaceutical composition for treating a cancer, comprising a bis(benzylidene-benzenamine)disulfide represented by formula III:

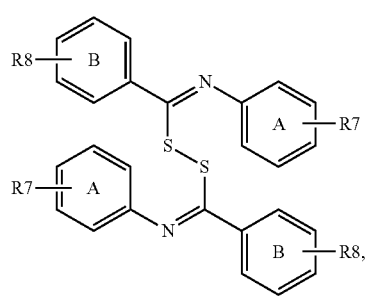

wherein the ring A has four sequentially bound carbon atoms, respectively bound with four R7s, each R7 is one selected from the group consisting of $CH_3$, $C_2H_5$, $C_3H_7$, $C_4H_9$, $C_5H_{11}$, $C_6H_{13}$, a nitrite $CF_3$, and a halide, the ring B has a para-carbon atom and a meta-carbon atom respectively bound with two R8s, and each R8 is one selected from the group consisting of $CH_3$, $C_2H_5$, $C_3H_7$, $C_4H_9$, $C_5H_{11}$, $C_6H_{13}$, a nitrite, $CF_3$, a halide, $OCH_3$, $OC_2H_5$, $OC_3H_7$, $OC_4H_9$, $OC_5H_{11}$, and $OC_6H_{13}$.

4. The pharmaceutical composition according to claim 3, wherein the halide is one selected from the group consisting of fluoride, chloride, bromide and iodine.

5. A preparation method of a pharmaceutical composition for treating a cancer, wherein the pharmaceutical composition comprises a bis(benzylidene-benzenamine)disulfide, the method comprising a step of:
synthesizing the bis(benzylidene-benzenamine)disulfide from two thiobenzamides with an oxidizing reagent, wherein each of the two thiobenzamides is represented by formula IV:

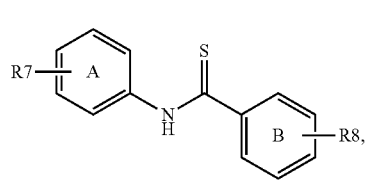

wherein the ring A has four sequentially bound carbon atoms, four R7s are respectively bound with the four carbon atoms, each R7 is one of a first electron-withdrawing group (EWG) and a hydrogen, the ring B has a para-carbon atom and a meta-carbon atom, two R8s are respectively bound with the para-carbon atom and the meta-carbon atom, and each R8 is one selected from the group consisting of a second EWG, an electron-donating group (EDG) and a hydrogen.

6. The preparation method according to claim 5 further comprising a step of forming a disulfide bond between the two thiobenzamides.

7. The preparation method according to claim 5, wherein the oxidizing reagent is one selected from the group consisting of 2,3-dichloro-5,6-dicyanobenzoquinone (DDQ), cerium(IV)ammonium nitrate (CAN), Dess-Martin periodinane (DMP) and phenyliodine(III) bis(trifluoroacetate) (PIFA).

8. The preparation method according to claim 7, wherein the oxidizing reagent is dissolved in a solvent being selected from the group consisting of dichloromethane, methanol and acetonitrile.

9. The preparation method according to claim 5, wherein the synthesizing step is performed at 0° C. to 30° C. for 20 minutes to 120 minutes.

10. The preparation method according to claim 5, wherein the synthesizing step is performed at 0° C. to 28° C. within 20 minutes.

11. The preparation method according to claim 5, wherein the bis(benzylidene-benzenamine)disulfide is represented by formula III:

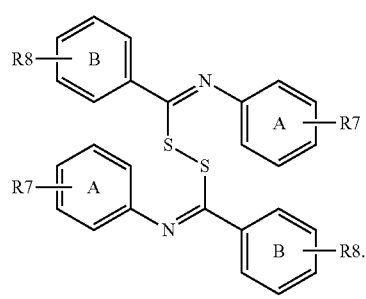

* * * * *